United States Patent
Adams

(10) Patent No.: US 8,361,138 B2
(45) Date of Patent: Jan. 29, 2013

(54) BRAIDED OCCLUSION DEVICE HAVING REPEATING EXPANDED VOLUME SEGMENTS SEPARATED BY ARTICULATION SEGMENTS

(75) Inventor: Daniel O. Adams, Long Lake, MN (US)

(73) Assignee: AGA Medical Corporation, Plymouth, MA (US)

( * ) Notice: Subject to any disclaimer, the term of this patent is extended or adjusted under 35 U.S.C. 154(b) by 609 days.

(21) Appl. No.: 11/881,026

(22) Filed: Jul. 25, 2007

(65) Prior Publication Data

US 2009/0025820 A1   Jan. 29, 2009

(51) Int. Cl.
*A61F 2/06* (2006.01)
(52) U.S. Cl. .................................. 623/1.15
(58) Field of Classification Search ............. 623/1.11, 623/1.15, 1.18–1.19, 1.22, 1.3, 1.32, 1.53, 623/903; 606/200, 108, 191
See application file for complete search history.

(56) References Cited

U.S. PATENT DOCUMENTS

| 3,874,388 A | 4/1975 | King et al. |
| 4,007,743 A | 2/1977 | Blake |
| 4,456,000 A | 6/1984 | Schjeldahl et al. |
| 4,619,246 A | 10/1986 | Nielsen |
| 4,836,204 A | 6/1989 | Landymore et al. |
| 4,917,089 A | 4/1990 | Sideris |
| 4,921,484 A | 5/1990 | Hillstead |
| 4,991,602 A | 2/1991 | Amplatz et al. |
| 5,064,435 A | 11/1991 | Porter |
| 5,067,489 A | 11/1991 | Lind |
| 5,108,420 A | 4/1992 | Marks |
| 5,171,259 A | 12/1992 | Inoue |
| 5,334,217 A | 8/1994 | Das |

(Continued)

FOREIGN PATENT DOCUMENTS

| WO | WO 9410936 | 5/1994 |
| WO | WO 9817183 | 4/1998 |

(Continued)

OTHER PUBLICATIONS

Benson, L., "Catheter Closure of the Ductus Arteriosus", Transcatheter Therapy in Pediatric Cardiology, Wiley-Liss 1993, two cover pages and pp. 321-333.

(Continued)

*Primary Examiner* — Ryan Severson
*Assistant Examiner* — Ashley Cronin
(74) *Attorney, Agent, or Firm* — Alston & Bird LLP

(57) ABSTRACT

The present invention provides a flexible, low profile vascular occlusion device having large volume filling capability and high metal content for fast occlusion, of the type fabricated from braided tubular metal fabric having an expanded preset configuration and an elongated collapsed reduced diameter configuration for delivery through a catheter to a treatment site and shaped to create an occlusion of an abnormal opening in a body organ or vessel, the woven metal fabric having a memory property whereby the medical device tends to return to said expanded preset configuration when unconstrained. The device further includes a first shape formed from the braided tubular fabric consisting of a repeating pattern of expanded volume segments separated by small diameter articulation segments and a second overall device shape comprised of the first shape formed about itself in various shapes to occlude a vessel. In one embodiment a shaping wire contained coaxially within the tubular braid, provides or assists in the formation of the second overall device shape.

40 Claims, 4 Drawing Sheets

U.S. PATENT DOCUMENTS

| | | | |
|---|---|---|---|
| 5,382,259 A * | 1/1995 | Phelps et al. | 606/151 |
| 5,451,235 A | 9/1995 | Lock et al. | |
| 5,456,693 A | 10/1995 | Conston et al. | |
| 5,466,242 A | 11/1995 | Mori | |
| 5,522,822 A | 6/1996 | Phelps et al. | |
| 5,624,461 A | 4/1997 | Mariant | |
| 5,725,552 A | 3/1998 | Kotula et al. | |
| 5,749,891 A | 5/1998 | Ken et al. | |
| 5,749,894 A | 5/1998 | Engelson | |
| 5,797,953 A | 8/1998 | Tekulve | |
| 5,911,731 A | 6/1999 | Pham et al. | |
| 5,944,738 A | 8/1999 | Amplatz et al. | |
| 5,964,797 A | 10/1999 | Ho | |
| 6,013,084 A * | 1/2000 | Ken et al. | 606/108 |
| 6,024,765 A | 2/2000 | Wallace et al. | |
| 6,033,423 A | 3/2000 | Ken et al. | |
| 6,059,812 A | 5/2000 | Clerc et al. | |
| 6,090,125 A | 7/2000 | Horton | |
| 6,123,715 A | 9/2000 | Amplatz | |
| 6,231,573 B1 | 5/2001 | Amor et al. | |
| 6,267,775 B1 | 7/2001 | Clerc et al. | |
| 6,322,576 B1 | 11/2001 | Wallace et al. | |
| 6,368,339 B1 | 4/2002 | Amplatz | |
| 6,599,308 B2 | 7/2003 | Amplatz | |
| 6,660,020 B2 | 12/2003 | Wallace et al. | |
| 6,746,461 B2 | 6/2004 | Fry | |
| 6,860,893 B2 | 3/2005 | Wallace et al. | |
| 6,994,717 B2 | 2/2006 | Konya et al. | |
| 7,326,225 B2 | 2/2008 | Ferrera et al. | |
| 2004/0098095 A1 * | 5/2004 | Burnside et al. | 623/1.13 |
| 2004/0098116 A1 | 5/2004 | Callas et al. | |
| 2005/0267510 A1 | 12/2005 | Razack | |
| 2006/0052823 A1 | 3/2006 | Mirizzi et al. | |
| 2006/0241690 A1 | 10/2006 | Amplatz et al. | |
| 2006/0241747 A1 | 10/2006 | Shaoulian et al. | |
| 2007/0265656 A1 * | 11/2007 | Amplatz et al. | 606/200 |
| 2009/0018562 A1 * | 1/2009 | Amplatz et al. | 606/157 |

FOREIGN PATENT DOCUMENTS

| | | |
|---|---|---|
| WO | WO 9829042 | 7/1998 |

OTHER PUBLICATIONS

Rao, P. S., and Sideris E. B., "Transcatheter Closure of Heart Defects: Role of Buttoned Devices", Transcatheter Therapy in Pediatric Cardiology, Wiley-Liss 1993, two cover pages and pp. 349-369.

Lock, J. E., Rome J. J., Davis, R., Van Praagh, S., Perry S. B., Van Praagh, R. and Keane, J. F., "Transcatheter Closure of Atrial Septal Defects", Circulation, vol. 79, No. 5, May 1989, pp. 1091-1099.

International Search Report and Written Opinion from International Application No. PCT/US07/22568 mailed May 8, 2008.

International Search Report and Written Opinion from International Application No. PCT/US2009/066964 mailed Feb. 4, 2010.

* cited by examiner

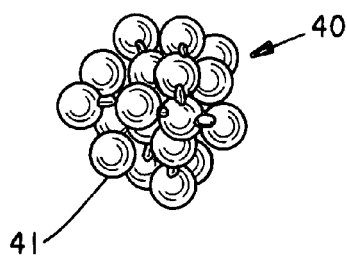
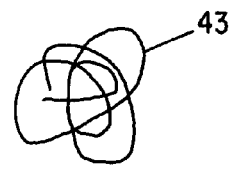
FIG. 6A    FIG. 6B
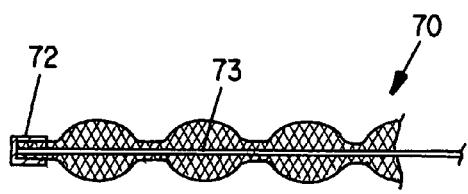
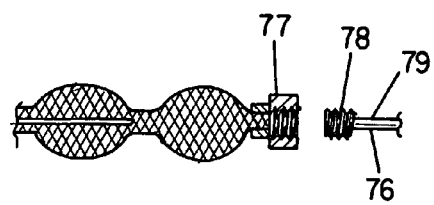
FIG. 7
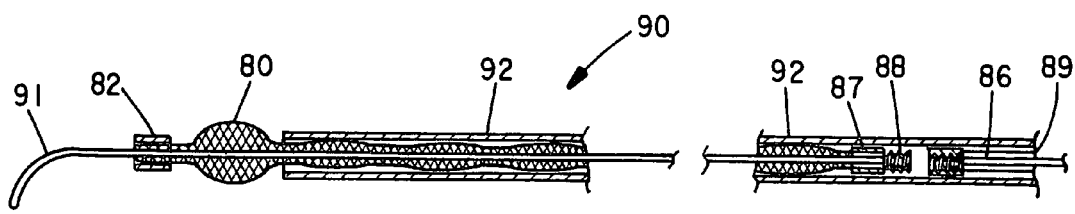
FIG. 8

BRAIDED OCCLUSION DEVICE HAVING REPEATING EXPANDED VOLUME SEGMENTS SEPARATED BY ARTICULATION SEGMENTS

BACKGROUND OF THE INVENTION

I. Field of the Invention

The present invention generally relates to intravascular devices for treating certain medical conditions and, more particularly, relates to intravascular occlusion devices for selective occlusion of a vessel, channel, lumen or cavity anywhere in the body's circulatory system where it is desired to stop the flow of blood. The devices made in accordance with the invention are particularly well suited for delivery through a small diameter flexible catheter or the like to a remote location treatment site in a patient's vascular system within a patient's body to occlude the site quickly by providing a high metal to volume ratio. The device can have a high ratio of delivery length to deployed length and can reach locations more tortuous than conventional occlusion devices.

II. Description of the Related Art

A wide variety of intravascular devices are used in various medical procedures. Certain intravascular devices, such as catheters and guidewires, are generally used simply to deliver fluids or other medical devices to specific locations within a patient's body, such as a selective site within the vascular system. Other, frequently more complex, devices are used in treating specific conditions, such as devices used in removing vascular occlusions or for treating vascular defects such as aneurysms and the like.

In certain circumstances, it may be necessary to occlude a patient's vessel, lumen, channel, hole or cavity such as to stop blood flow therethrough.

Mechanical embolization devices are well known in the art and sold commercially for occlusion of vessels in various locations within the vasculature. U.S. Pat. No. 6,123,715 by Amplatz and U.S. Pat. No. 5,725,552 by Kotula disclose intravascular occlusion devices fabricated from Nitinol braided metal fabric which are heat set in molds to an expanded shape, but which can be compressed for delivery through a catheter to a treatment site, whereby the device, when urged out of the delivery catheter, self expands within the vasculature to occlude blood flow at the treatment site. The details of the various designs and configurations as well as methods of fabricating and using the devices are detailed in the aforementioned patents and that are hereby incorporated in total herein by reference.

Although the occlusion devices described by Amplatz and Kotula patents are quite effective, there are significant improvements that can be made. In the Amplatz U.S. Pat. No. 5,725,552, there is shown, in FIGS. 5A and 5B, an elongated braided metal fabric vascular occlusion device which incorporates two spaced apart expanded diameter disk elements between the ends. The disk elements are intended to engage the vessel inside surface to cause thrombosis of the vessel by interaction of the blood and the Nitinol wire fabric. The disk elements are also sized in their freely expanded state to be somewhat larger in diameter than the vessel inside diameter to help anchor the device. This imparts a load from the Nitinol braid's desire to expand larger to be imparted against the wall defining a body lumen to secure the device in place.

The disks are preferably spaced apart to stabilize the device within the vessel and prevent the device from turning off axis to the vessel. The device is elongated for delivery through a catheter lumen by pulling the end wire clamps away from each other. This action draws the device diameter down for insertion into the catheter. A delivery system consisting of an elongated wire with a threaded end which engages a mating threaded end on one of the wire end clamps on the device allows the device to be pushed through the delivery catheter. As the device emerges out the distal end of the catheter, the device self-expands to its memorized pre-determined heat set shape. The treaded connection allows control of the device for retrieval, repositioning, or to be selectively released once the device is properly placed in the vessel.

The disk diameters in their relaxed state are somewhat larger in diameter than the delivery catheter lumen diameter. The stiffness of the disks and their large diameter contribute to the force required to push the device through delivery catheter. Additionally, since the device is being pushed from the proximal end rather than pulled from the distal end, the device is slightly compressed which leads to a small amount of outward expansion and also contributes to the delivery force required. To reduce this load, the lumen of the delivery catheter may have to be increased. However, this causes the delivery catheter to be stiffer and less able to easily pass through tortuous vessels than otherwise. Also the amount of metal density for a given volume occupied can affect the rate at which thrombosis will occur to occlude the vessel. Generally, the more metal exposed to the blood flow, the faster the thrombosis rate; also, more metal typically equates to a lower rate of device recanalization after implant. The Amplatz device has a relatively low metal to volume ratio compared to the inventive design described herein and therefore often uses added polyester fiber to enhance the thrombosis rate.

Another prior art occlusion device is described in U.S. Pat. No. 6,033,423 by Ken et. al "Multiple Layered Occlusive Coils". This patent describes a vaso-occlusive device intended for occluding a vessel or an aneurysm, primarily in the brain. The occlusive device is a small diameter coiled wire, preferably 0.010-0.018 inch in diameter made preferably of a shape memory material such as Nitinol. The coiled wire is wrapped about itself and heat set to retain a three dimensional volume occupying shape to occlude a vessel. The coil is stretched to reduce its profile to that of the coil itself for introduction through a catheter. The coils are very flexible and can be passed through small diameter tortuous vessels, such as are encountered in the brain via a micro catheter. Because the coil diameter must be maintained small for passage through a small diameter catheter, the length of the coil to fill a given volume is quite long. The practicality of using such small coils in larger volumes, such as aneurysms found outside the neuro-vasculature or in a cavity of significant volume is reduced due to the small occupying volume of these micro coils.

Accordingly, it is advantageous to provide an improved vasculature occlusion device which offers better volume filling capability for a given length of implant, smaller delivery catheter diameter than conventional prior art systems, lower forces for advancement of the device through the delivery catheter, enhanced ability to traverse a tortuous vessel, and an increased rate of thrombosis by providing a higher metal to volume ratio.

In addition it would be advantageous in certain circumstances to be able to deliver the device using an "over the wire" approach, as well known in the angioplasty catheter field. It would also be beneficial to have a greater shape retention force by the addition of an optional shape retention wire to assist or provide the vessel occlusive device final shape.

SUMMARY OF THE INVENTION

The present invention provides an inventive solution to the above problems with the prior art. By using a braided tubular fabric made from a shape memory material, such as Nitinol, and the same methods of fabrication, molding and heat treatment and delivery as described by U.S. Pat. Nos. 6,123,715 by Amplatz and 5,725,552 by Kotula et. al., the present invention provides a flexible, low profile vascular occlusion device having a large volume filling capability and high metal content for fast occlusion. As in the referenced patents, braided tubular metal fabric having an expanded preset configuration and an elongated collapsed reduced diameter configuration for delivery through a catheter to a treatment site is shaped to create an occlusion of an abnormal opening in a body organ or vessel. The woven metal fabric has a memory property, whereby the medical device tends to return to said expanded preset configuration when unconstrained. The occlusive device further includes a first shape formed from the braided tubular fabric consisting of a repeating pattern of expanded diameter or volume segments separated by small diameter articulation segments and a second overall device shape comprised of the first shape formed about it self in various volumetric shapes to occlude a vessel.

In another embodiment, a shaping wire is contained coaxially within the tubular braid, and provides or assists in the formation of the second overall final device shape.

The present invention is well suited for the selective occlusion of a vessel, lumen, channel, or cavity. Several examples, without limitation, are an aneurysm, a left atrial appendage for patients with left atrial fibrillation, an Arterial Venous Fistula (AVF) or an Arterial Venous Malformation (AVM) or any vessel needed to be occluded to prevent blood flow there through. Other possibilities are treatment of an Atrial Septal Defect (ASD), a Ventricular Septal Defect (VSD), a Patent Foreman Ovale (PFO), or a Patent Ductus Arteriosus (PDA).

When forming these intravascular occlusive devices from a resilient metal fabric, a plurality of resilient strands is provided, with the wires being formed by a braiding machine to create a resilient material which can be heat treated to substantially set a desired shape. This braided fabric is then deformed to generally conform to a molding surface of a molding element and the braided fabric is heat treated in contact with the surface of the molding element at an elevated temperature to form a first molded shape. The first molded shape in space in the preferred embodiment is a repeating expanded diameter or volume segment with an ovaloid or spherical shape and with a separation between adjacent expanded volumes consisting of the braid formed in a small diameter to function as articulation segments between the expanded volumes. The time and temperature of the heat treatment is selected to substantially set the braided fabric in its deformed state. After the heat treatment, the fabric is removed from contact with the molding element and will substantially retain its shape in an unstressed state. The elongate molded element is further configured to a second heat treated shape by winding the elongate element about itself into any one of a number of three dimensional shapes to be further discussed in the following detailed description. The braided fabric heat treated a second time defines an expanded state of a medical device which can be deployed through a catheter into a channel in a patient's body and placed at a desired target site.

In another embodiment of the invention the first heat treatment braid shape is achieved as previously described above, but the final device shape is achieved by use of a shape memory wire sized to be placed through the first shaped heat treatment braid and heat treated as an assembly in a second shape desired of the final device braid central axis. In this embodiment, the wire is inserted into the first shaped heat treated braid prior to the second heat treatment and the distal end of the braid is attached to the distal end of the wire at the braid distal end clamp. The proximal end of the wire free floats within the proximal braid. During use, when the device is pushed out the distal end of a delivery catheter, the shaped wire and braid will assume its memorized final device shape.

Alternatively, the shape memory wire may be heat treated separately in the final device or second shape and then inserted into the braid having a first shape. The composite device will take on the final device's second shape based on the shaped wire being stronger in shape retention than the articulation segments of the braid.

Embodiments of the present invention provide specific shape improvements over prior art medical devices which may be made in accordance with the present invention to address occlusion of vessels having specific anatomical conditions. Such devices of the invention are formed of a braided metal fabric and have an expanded configuration and a collapsed configuration. In use, a catheter can be positioned in a channel in a patient's body and advanced to position the distal end of the catheter adjacent a treatment site for treating a physiological condition. A medical device, formed in a predetermined shape, and made in accordance with the process outlined above, can be collapsed by stretching the ends apart and can be inserted into the lumen of the catheter. In use, the device is urged through the catheter and out the distal end, whereupon, due to its memory property, it will tend to substantially return to its expanded state adjacent the treatment site.

In accordance with a first of these embodiments, the occlusive device is shaped into a helix or coil with a length to give it longitudinal stability and adequate anchoring within a vessel or cavity. The device is sized somewhat larger than the vessel or cavity for which it is intended to provide an outward expansion force against the wall of the vessel or cavity to retain the device in place and prevent device embolization. Alternative shapes involve a coil inside a coil, to give a more solid filling of the vessel or alternatively a device shaped into coils that alternate in diameter from small to larger. Another alternative is a device final shape that is somewhat spherical. There are few, if any, limitations to the shape of device that can be fabricated. Devices may be fabricated to take the shape of an aneurysm of any size and shape. Alternatively, it can be sized to fit a left atrial appendage or other vascular anomaly.

One embodiment provides a means for over the wire delivery while the occlusive device is within the delivery catheter.

The inventive occlusive device will occlude a vessel, channel, lumen, or cavity quickly due the high metal to volume filled ratio and due to the volume occupying expanded diameter portions of the braid that interface with the blood and also restrict blood flow. The device can be stretched for delivery through a small diameter catheter and, due to its flexible nature, can be passed easily through tortuous pathways within the human body.

BRIEF DESCRIPTION OF THE DRAWINGS

FIG. 6A is a side view of the inventive device in a shape approximating a sphere.

FIG. 6B is a side view of a shape memory wire that may be used as an alternative embodiment component to create the shape as illustrated in FIG. 6A.

FIG. 7 is a partial cross-sectional view of an alternative embodiment of the inventive device including a shaped memory wire internal to the braid to assist in shaping the device.

FIG. 8 is a partial cross-sectional view of another alternative embodiment of the inventive device adapted for over the wire delivery.

DETAILED DESCRIPTION OF THE PREFERRED EMBODIMENTS

Figure 1:
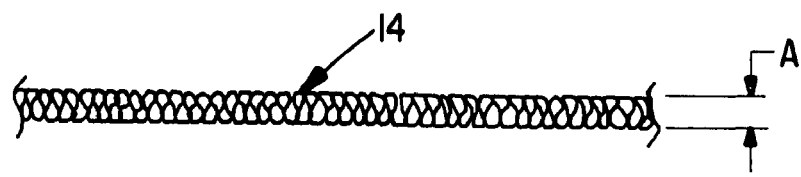
FIG. 1 is a side view of a section of a braided tubular member of a shape memory wire construction prior to its being shaped and heat treated.

The present invention provides an improved percutaneous catheter directed intravascular occlusion device for use in the vasculature in patients' bodies, such as blood vessels, channels, lumens, a hole through tissue, cavities and the like. In forming a medical device of the invention, a metal fabric is formed of a plurality of wire strands having a predetermined relative orientation between the strands.

The metal strands define two sets of essentially parallel generally helical strands, with the strands of one set having a "hand", i.e. a direction of rotation, opposite that of the other set. This defines a generally tubular fabric, known in the fabric industry as a tubular braid. The Amplatz and Kotula patents previously discussed describe medical devices and the methods of fabrication of such devices in great detail so only general discussion is provided.

The pitch of the wire strands (i.e. the angle defined between the turns of the wire and the axis of the braid) and the pick of the fabric (i.e. the number of wire crossovers per unit length) may be adjusted as desired for a particular application. The wire strands of the metal fabric used in the present method should be formed of a material which is both resilient and which can be heat treated to substantially set a desired shape. Materials which are suitable for this purpose include a cobalt-based low thermal expansion alloy referred to in the field as Elgeloy, nickel-based high temperature high-strength "super-alloys" commercially available from Haynes International under the trade name Hastelloy, nickel-based heat treatable alloys sold under the name Incoloy by International Nickel, and a number of different grades of stainless steel. The important factor in choosing a suitable material for the wires is that the wires retain a suitable amount of the deformation induced by the molding surface when subjected to a predetermined heat treatment.

Another class of materials which meet these qualifications is so-called shape memory alloys. One particularly preferred shape memory alloy for use in the present method is a nickel-titanium alloy called Nitinol®. NiTi alloys are also very elastic—they are said to be "superelastic" or "pseudoelastic". This elasticity will help a device of the invention return to a present expanded configuration for deployment when no longer constrained, say, in a lumen of a delivery catheter.

In forming a medical device in keeping with the invention, an appropriately sized piece of the metal fabric is cut from the larger piece of fabric which is formed, for example, by braiding wire strands to form a long tubular braid. When cutting the fabric to the desired dimensions, care should be taken to ensure that the fabric will not unravel.

One can solder, braze, weld or otherwise affix the ends of the desired length together (e.g. with a biocompatible cementitious organic material) before cutting the braid.

Once an appropriately sized piece of the metal fabric is obtained, the fabric is deformed to generally conform to a surface of a molding element. Deforming the fabric will reorient the relative positions of the strands of the metal fabric from their initial order to a second, reoriented configuration. The shape of the molding element should be selected to deform the fabric into substantially the desired shape.

Once the molding element is assembled with the metal fabric generally conforming to a molding surface of that element, the fabric can be subjected to a heat treatment while it remains in contact with that molding surface. Suitable heat treatments of Nitinol wire to set a desired shape are well known in the art. It has been found that holding a Nitinol fabric at about 500° C. to about 550° C. for a period of about 1 to about 30 minutes, depending on the softness or hardness of the device to be made, will tend to set the fabric in its deformed state, i.e. wherein it conforms to the molding surface of the molding element. At lower temperatures the heat treatment time will tend to be greater (e.g. about one hour at about 350° C.) and at higher temperatures the time will tend to be shorter (e.g. about 30 seconds at about 900° C.).

After the heat treatment, the fabric is removed from contact with the molding element and will substantially retain its shape after being deformed. Attention is now directed to FIG. 1 which illustrates a braided tube as braided prior to any shape forming a heat treating process. The wires are preferably made of Nitinol alloy and may range from 0.001-0.006 inch in diameter, preferably 0.0015-0.003 inch in diameter. The number of wires that make up the braid may be from 8 to 144, preferably 8-32. The braid is formed over a 3-4 mm diameter mandrel for the smallest braid using 8-16 wires and larger mandrel for more wires or larger diameter wires.

Figure 2A:
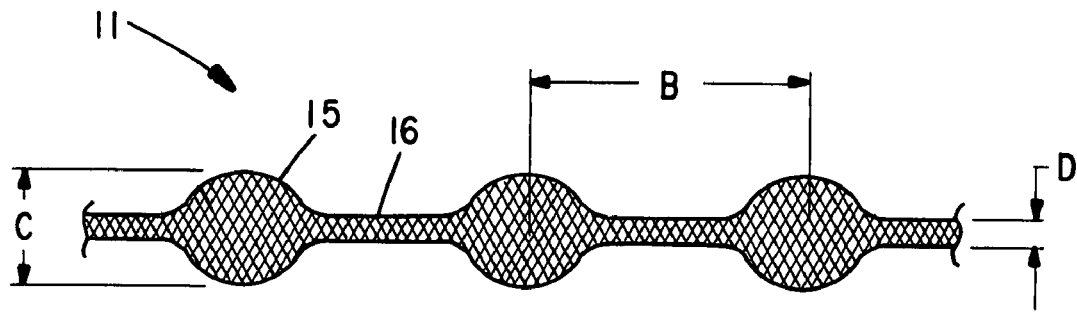
FIG. 2A is a side view of one example of the tubular member of FIG. 1 after shaping in a mold and heat treatment to set memory.
Figure 2B:
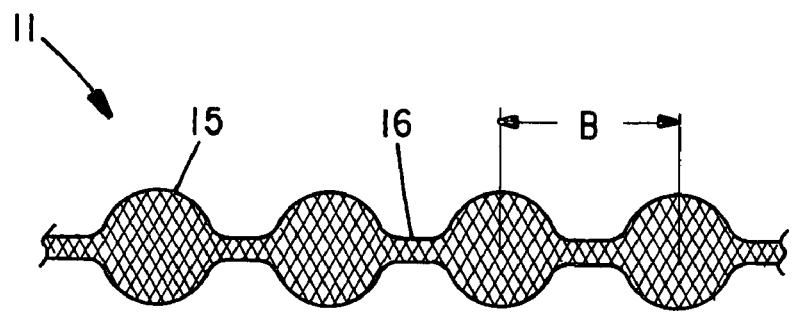
FIG. 2B is a side view of another example of the tubular member of FIG. 1 after shaping in a mold and heat treatment.

FIG. 2A illustrates the first heat set shape of the inventive device 11. The first heat set molded shape consists of the braided tubular member 14 expanded to a larger diameter or volume segment 15 in a repeating pattern with a reduced braid diameter segment 16 between adjacent expanded segments 15. The expanded segments 15 serve as the volume filling aspect of the invention and the reduced diameter portions 16 serve as articulation segments to allow the tubular member to be wound upon it self into various configurations. FIG. 2B indicates a pitch B between repeating segments different than that indicated in FIG. 2A.

There is no requirement that the original braided tube be made to a specific initial diameter relative to the formed first shape. For example the initial braided tube could be larger or smaller than the first heat set shape, provided the desired shape is able to be formed and provided the device can be drawn down for insertion into a delivery catheter and the helix angle of the braid in the expanded segment has the desired outward resistance to collapse.

There is also no specific requirement for the pitch between expanded segments or between articulation segments be uniform. If fact, for certain configurations to be formed in the final device shape it may be highly desirable to alter the spacing of either type of segment at a particular position along the device length as will be discussed later in more detail.

Preferably the expanded segments are either ovaloid or spherical in shape although they may be any other shape as well, and the expanded shape may have a variable volume or diameter along the device length.

As shown in FIG. 7, the ends of this braided metal fabric device 70 are welded or clamped together with clamps 72 and 77 to avoid fraying. Of course the ends may alternately be held together by other means readily known to those skilled in the art. The clamp 77 tying together the wire strands at the proximal end of device 70 also serves to connect the device to a delivery system 76. In the embodiment shown, the clamp 77 is generally cylindrical in shape and has a recess for receiving the ends of the metal fabric to substantially prevent the wires comprising the woven fabric from moving relative to one another. The clamp 77 also has a threaded surface within the recess. The threaded recess is adapted to receive and engage the threaded distal end 78 of a delivery device 79. The distal clamp 72 also has a recess for receiving the distal wire ends. The clamps may optionally be fabricated from a radiopaque material such as platinum-iridium alloy or may be stainless steel or other well known materials.

FIG. 8 represents an occluder device adapted for over-the-wire delivery. Optionally, but not considered a requirement, the device 90 as shown in FIG. 8, could be configured with a clamp member assemblies 82 and 87 at both wire ends whereby the assembly comprises a hollow inner and outer sleeve. The distal outer clamp member is sized with an inside diameter sufficient to accommodate the braid wire ends surrounding the inner clamp member prior to swaging or alternatively may be bonded between the clamp members or welded in place. The inner clamp member is tubular and is sized with an inside diameter able to freely pass a guidewire 91 therethrough, which typically is 0.010-0.018 inch diameter, preferably 0.010 inch wire or cable. The proximal outer clamp member is shown with external threads 88 to reversibly connect to the delivery system 89, which is preferably a nylon block co-polymer, such as Pebax, with 0.001 inch. stainless steel braided wire over the Pebax inner tube extrusion, followed by another outer layer of Pebax to cover the braid. Such construction is typical in intravascular guide catheters where flexibility and torque transmission are needed. The Pebax inside diameter is sufficient to easily pass the guidewire 91.

Attention is next directed to FIGS. 3-6A and 6B. Discussion now is in regard to a heat set second or final device shape. Four examples (no limitation) of specific device final shapes are discussed, as well as three main methods of device fabrication. In the first general method of forming the second or final device shape, the device of, for example FIG. 2A which has a first formed shape that is wrapped about itself into a second or final device shape and held in place during a second heat setting process to retain this shape upon cooling and removing from the mold.

In a second general method of device fabrication, a separate shape memory wire 73 (FIG. 7) of preferably between 0.005-0.010 inch diameter Nitinol alloy (range of 0.003-0.020 inch) is placed coaxially within the braid having a first formed shape, and the braid and wire assembly are placed in a mold which holds the assembly wire in the shape of the axis of the braided device's desired final shape. In this design, either before or optionally after the assembly heat treatment, the wire 73 and the distal braid wire ends are clamped into the distal clamp 72 by crimp, bond, weld or other well known means. The proximal end of the wire will match the braid length or be just short of the braid length when the braid is in its free expanded state. The proximal end of the wire free floats within the proximal braid portion to allow the braid to lengthen for placement in a delivery catheter as shown in FIG. 7.

In a third general method of device fabrication, the shape memory wire may be heat treated separately in a mold constricting the wire to the final device or second shape. After heat treatment has memorized the desired shape into the wire, the braid with its first heat set established shape is threaded over the wire until the distal end of the wire and the distal end of the braid are aligned. The wire 73 and the distal braid end wires are clamped into the distal clamp 72 by crimp, bond, weld or other well-known means. The proximal end of the wire will match the braid length or be just short of the braid length when the braid is in its free expanded state. The proximal end of the wire free floats within the proximal braid portion to allow the braid to lengthen for placement in a delivery catheter as shown in FIG. 7. The proximal braid wire ends are clamped into the proximal clamp 77. The composite device will take on the final device's second shape based on the shaped wire being stronger in shape retention than the articulation segments of the braid.

Figure 3A:
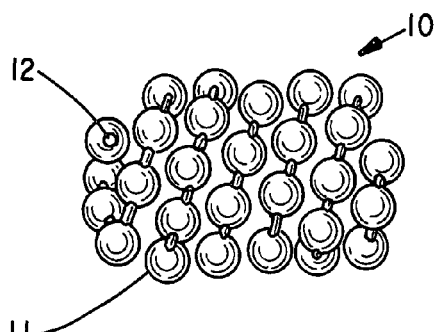
FIG. 3A is a side view of the inventive device in a simple coiled shape.
Figure 3B:
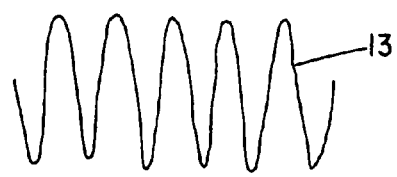
FIG. 3B is a side view of a shape memory wire that may be used as an alternative embodiment component to create the shape as illustrated in FIG. 3A

In FIG. 3A the occlusion device's second shape consists of a coil or spiral winding of the first shape for a given length and diameter. The length should be minimally about twice the diameter for stability within a vessel. This device shape may be made using any of the first, second or third general fabrication methods. FIG. 3B illustrates the longitudinal view of the shape of the separate heat set shaping wire 13 that can be used to fabricate the device in 3A using the second or third general fabrication method. Optionally, the ends of the coil can be shaped such that the last few expanded segments 15 are curved in a smaller radius to occlude the entrance and exit of the coil to further restrict flow. The shapes as shown in FIGS. 3-5 would be particularly suitable for occluding a tubular vessel and have the ability to adapt to a curve or bend in a vessel. The shape in FIG. 6 could be used in a vessel, but may be adaptable to occluding a cavity, such as the left atrial appendage (LAA) or perhaps an aneurysm.

Figure 4A:
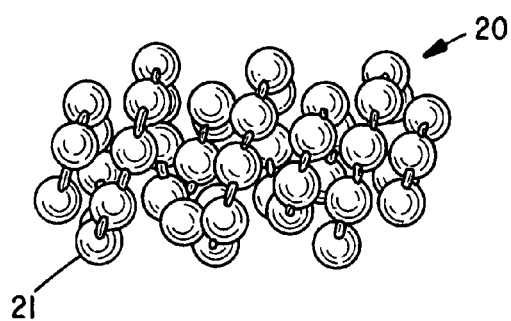
FIG. 4A is side view of an alternative embodiment of the inventive device having a coiled shape consisting of alternating smaller and larger diameter coils.
Figure 4B:
FIG. 4B is a side view of a shape memory wire that may be used as an alternative embodiment component to create the shape as illustrated in FIG. 4A.

In FIG. 4A, the occlusion device 20 second shape consists of a coil or spiral winding having alternating small and large diameters of the first shape for a given length. By alternating the diameters a more complete occlusion can be obtained for filling vessels having inside diameters greater than at least twice the diameter of the expanded volume segments 15. The coiled device length should be minimally about twice the diameter for stability within a vessel. This device shape may be made using any of the first, second or third general fabrication methods previously described. FIG. 4B illustrates the longitudinal view showing the shape of the separate heat set shaping wire 23 that can be used to fabricate the device in 4A using the second or third general fabrication method. Alternatively the device could have 3 or more alternating diameters for larger diameter vessels in relation to the expanded segment 15 diameter.

Figure 5A:
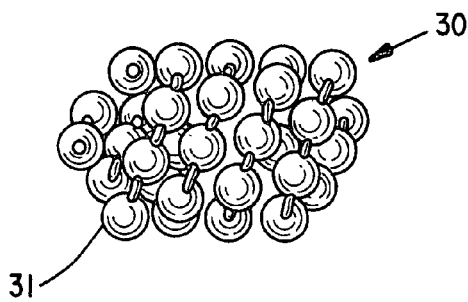
FIG. 5A is a side view of an alternative embodiment of the inventive device having a continuous coil with a small diameter on the inside of the device wrapped by a larger diameter coil.
Figure 5B:
FIG. 5B is a side view of a shape memory wire that may be used as an alternative embodiment component to create the shape as illustrated in FIG. 5A.

In FIG. 5A, the occlusion device 30 has a second shape consisting of a complete internal coil surrounded by an external coil. This provides a dense metal arrangement for occlusion of a vessel or cavity such as an aneurysm or left atrial appendage. The structure can be fabricated using any of the 3 general methods previously discussed and would fill vessels having a diameter at least 4 times larger than the expanded segments 15. FIG. 5B illustrated a longitudinal view showing the shape of the separate fabrication heat set shaping wire 33 that can be used to fabricate the device in 5A using the second or third general fabrication method. The device can be configured to first deploy the inside coil and then the outside coil or vice versa. Additionally, it may be desirable to deploy both coils distal to proximal by providing a long articulation segment 16 which extends the length of the first coil proximal end to the distal end of the second coil to allow the second coil to also form distal to proximal.

FIG. 6A illustrates a shape of an occlusion device 40 which has a second shape that is somewhat spherical in shape. The shape is fabricated by wrapping the device of the first heat set shape about itself into the desired shape and then heat setting the wrapped shape while being held in place by a mold or other retaining means. As mentioned above, the winding pattern can be selected as desired to form a shape such as an ovaloid for perhaps an aneurysm or the shape of a cavity to be filled, such as a left atrial appendage.

FIG. 6B illustrates a separate heat shaped wire that may be used to fabricate the device as shown in FIG. 6A using the second or third general fabrication method.

Since a great variety of vessels, aneurysm or cavity sizes may need to be filled, the choice of braid wire diameter, number of wires in the braid and the size of the expanded segments can be chosen relative to the vessel size. It would be preferable that the expanded segment be small in relation to the vessel or cavity maximum width. For example, the expanded diameter segment should be in the range of 0.4-0.1 (preferably 0.3-0.2) of the width of the vessel or cavity to be filled. The final size of the device should be sized to be slightly larger than the vessel or cavity to be filled so as exert an outward force of the vessel or cavity wall to adequately retain the device in place.

Depending on the desired final device shape, the articulation segment length may be altered to obtain the closest fit or nesting of the expanded segments against adjacent expanded segments. As shown in FIG. 5A, an outer coil rests against an inner coil. The articulation segment length of the second coil may be different from the inner coil to achieve best packing or nesting of expanded segments. This close nesting provides high metal density and improved flow restriction for quick occlusion (thrombosis) of the vessel.

Those skilled in the art will appreciate that in order to speed up the occlusion of the vessel device, the device may be coated with a suitable thrombogenic agent, filled with a polyester fiber or braided with an increased number of wire strands. The prior art devices have preferably used a polyester within the braided device. When placed internal to the braid, his fiber can easily collapse with the device for delivery through a catheter. The interwoven fiber, by attachment to the clot, retains the clot firmly within the device as it forms the occlusion.

FIG. 8 illustrates a delivery device that can be used to urge the occlusion device 10, 20, 30, or 40 through the lumen of a catheter 92 or long introducer sheath for deployment in a channel of the patient's body. When the device is deployed out the distal end of the catheter, the device will still be retained by the delivery device 79 or 89 in FIG. 7 or 8 respectively. Once the proper position of the device in the vessel is confirmed, the shaft of the delivery device can be rotated about its axis to unscrew the clamp 77 or 87 from the delivery device 79 or 89 respectively.

By keeping the occlusion device attached to the delivery means, the operator is still able to retract the device for repositioning if it is determined that the device is not properly positioned in a first attempt. This threaded attachment will also allow the operator to control the manner in which the device 10 is deployed out of the distal end of the catheter. When the device exits the catheter, it will tend to resiliently return to a preferred final expanded shape which is set when the fabric is heat treated. When the device springs back into this shape, it may tend to act against the distal end of the catheter, effectively urging itself distally beyond the end of the catheter. This spring action could conceivably result in improper positioning of the device. Since the threaded clamp 77 or 87 (FIG. 7 or 8) can enable the operator to maintain a hold on the device during deployment, the spring action of the device can be accommodated and the operator can control the deployment to ensure proper positioning.

FIG. 7 illustrates an occluder device fabricated by the second or third general method containing the separate heat set device shaping wire 73 fasted to the distal wire end clamp 72 by crimp, swage, adhesive, solder or other means. The proximal end of the wire 73 floats within the braid and is shorter than the braid when stretched for delivery through the catheter 92 (FIG. 8). The delivery device 79 has a wire or cable shaft 76 with an adapter 78 at the distal end with male threads that engage with internal threads on the wire clamp 77.

FIG. 8 illustrates a partial cut away of system 90 consisting of occlusion device 80 delivery device 89, a guidewire 91 and the delivery catheter 92. In this embodiment the device 80 has been modified in design for over-the-wire delivery. The proximal and distal end clamps 87 and 82 consist of an inner sleeve and outer sleeve. The inner sleeve has an inside diameter sized for a sliding fit over a guidewire. The outer sleeve is sized to fit over the end wires and over the inner sleeve. The end wires are placed between the two sleeves and are crimped, swaged, welded, or bonded in place to keep the wires from unraveling. The proximal clamp 87 contains threads 88 which mate with a threaded connection on the delivery device 89, which is preferably a nylon block co-polymer extruded tube, such as Pebax, reinforced with a 0.001 in. braided wire embedded in the Pebax during co-extrusion. Such construction is typical in guide catheters where flexibility and torque transmission are needed. Optionally, the delivery device may be a stainless steel coil fabricated from round or flat wire having a lumen sufficient to freely pass the guidewire and covered by a thin polymer tubing, such as a shrink wrap tubing, to contain the coil and provide torque transmission with flexibility and push force. A distal threaded connector is attached, as by welding or other means to the coiled distal end of the delivery device for reversible connection to the occlusive device 80. The coil shaft of the delivery device may be coated with PTFE to reduce friction between the coil and the guidewire. A small diameter hypotube may also be used as the shaft of a delivery device with the inside diameter sized to accept the guidewire passage there through.

Figure 9:
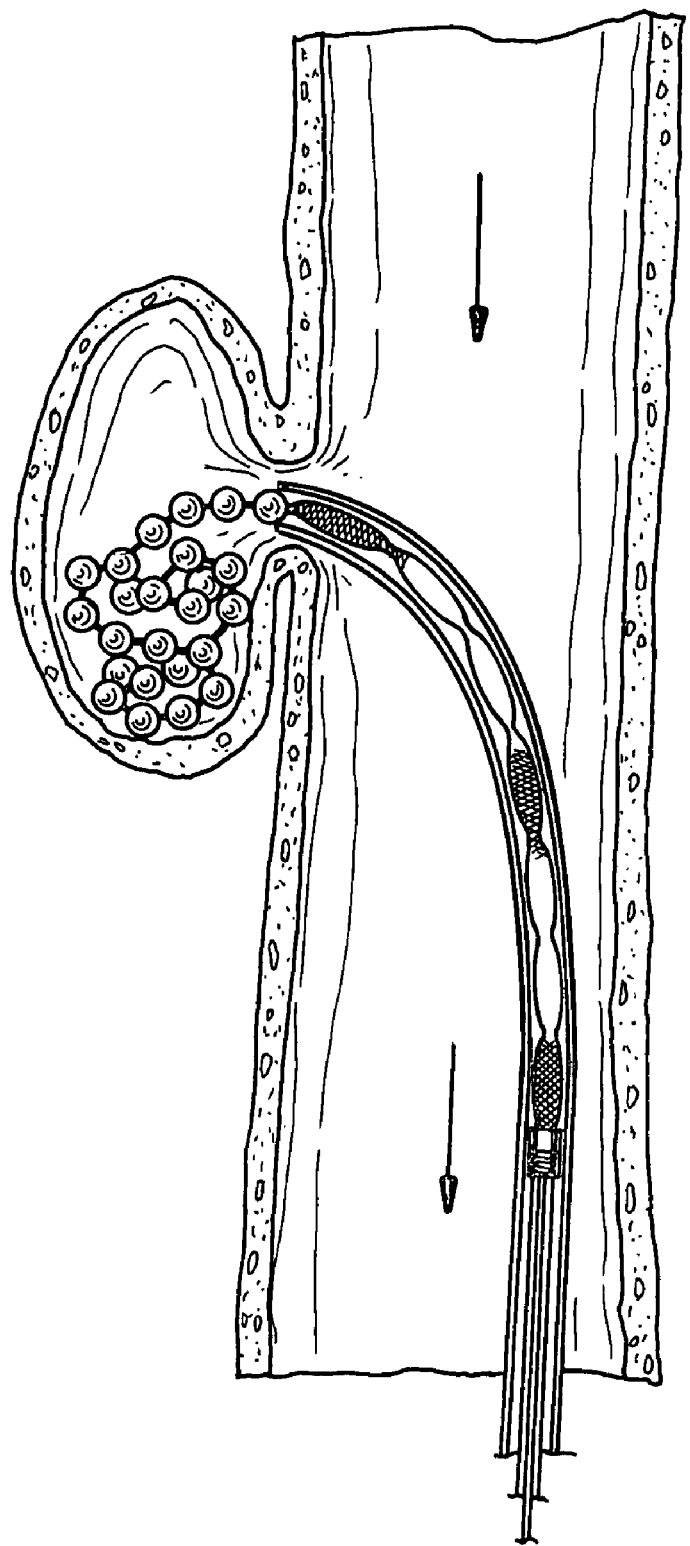
FIG. 9 is a cross-sectional view of an occluder of the present invention partially extending from the distal end of a delivery catheter filling a thoracic aortic aneurysm.

The delivery catheter may be a simple extruded tube preferably made of Pebax. The tubing has a lumen sized for passage of the occlusion device and the delivery device. The delivery catheter may have a shaped tip to allow a predetermined orientation to the occlusion device for delivery to an aneurysm as shown in FIG. 9. To improve the torque response of the delivery catheter for tip control, the Pebax tubing may have 0.001 stainless steel wire braided embedded in Pebax polymer, much like a guide catheter. In some cases, a guide catheter itself, or perhaps a diagnostic catheter or long sheath, may serve as the delivery device.

In use, the occlusion device 80 (FIG. 8) is connected to the delivery device 89 by threading the devices together. The proximal end of the delivery device 89 is back loaded into the distal end of the delivery catheter 92. The occlusive device 80 is stretched by this motion and drawn down in diameter and into the delivery catheter 92 proximal end. The system 90 may be shipped in this configuration for ease of use reasons. Access (typically via the femoral artery) to the arterial system is achieved by use of the Seldinger Technique as is when known. An arterial sheath is placed in the artery. In the case of an over-the-wire delivery, as shown in FIG. 8, a guidewire is first inserted through the sheath and into the artery. The proximal end of the guide wire is back loaded through the occlusion device distal clamp exposed a short amount out the distal end on the delivery catheter. The delivery catheter containing the occlusion device and delivery device is advanced over the guidewire, through the sheath and into the artery. The guidewire is advance and steered through the vasculature to the target location. The delivery catheter is advanced until the distal tip is positioned at the target site. The guide wire may be removed before advancement of the device 80 out the delivery catheter or may be withdrawn after the occlusion device is partially into the vessel or cavity to be filled. The device 80 is then advance by pushing on the delivery device 89 until the entire device 80 is positioned as desired. If the device is positioned correctly, the delivery device is unscrewed by rotation from the occlusion device and the delivery catheter and delivery device are withdrawn. If the device is not initially positioned correctly, the device 80 may be drawn back unto the delivery catheter 92 and a further attempt made to reposition the device as often as needed so long as the threaded connection is retained. Once the threaded connection is separated, the device can not be recaptured into the catheter 92.

In the case of a non-over-the wire device as shown in FIGS. 7 and 9, the delivery catheter may be advanced over a guidewire, as long as the occlusive device and attached delivery device are not pre-loaded into the catheter. Once the delivery catheter is positioned as desired the guide wire may be withdrawn from the body and the occlusive device and delivery device must be forward loaded into the proximal end of the delivery catheter. This may be accomplished by placement of a tear-away introducer sleeve over the distal end of the delivery device before connection to the occlusive device. The introducer sleeve has an outside diameter slightly smaller than the I.D. of the delivery catheter. The threaded connection is made between the occlusion device and the delivery device and the occlusive device is drawn into the tear-away sleeve. Once inside the sleeve the occlusive device can be piloted into the usual Luer connector leading to the lumen on the proximal end of the delivery catheter 92. Advancement of the delivery device delivers the occlusive device through the delivery catheter. The introducer sleeve may now be torn away from the delivery device and discarded. With the delivery catheter in position, the delivery device may be advanced to deliver the occlusive device to the target site for vessel or cavity being occluded.

Angiography is typically used in catheter based procedures to image the devices and catheters during delivery. The end clamps may be radiopaque or radiopaque markers may be added to the occlusive device if desired. Generally the amount of metal in these occlusive devices can be seen on fluoroscopy. Radiopaque dye may be used to determine when blood flow through the vessel or cavity has been stopped by thrombosis.

Although the device will tend to resiliently return to its initial expanded configuration (i.e. its shape prior to being collapsed for passage through the catheter), it should be understood that it may not always return entirely to that shape. For example, the device is intended to have a maximum outer diameter in its expanded configuration at least as large as and preferably larger than, the inner diameter of the lumen in which it is to be deployed. If such a device is deployed in a vessel having a small lumen, the lumen will prevent the device from completely returning to its expanded configuration. Nonetheless, the device would be properly deployed because it would engage the inner wall of the lumen to seat the device therein, as detailed above.

If the device is to be used to permanently occlude a channel or cavity in the patient's body, such as the devices 10, 20, 30, 40, 70, and 80 described above may be, one can simply disconnect the delivery system by reversing the reversible connection to the device and retract the catheter and delivery device from the patient's body. This will leave the medical device deployed in the patient's vascular system so that it may occlude the blood vessel or other channel in the patient's body.

While preferred embodiments of the present invention have been described, it should be understood that various changes, adaptations and modifications may be made therein without departing from the spirit of the invention and the scope of the appended claims.

The invention claimed is:

1. A method of making a medical device comprising:
   a) braiding a plurality of metal strands exhibiting a shape memory property into a tubular metal fabric to form a braided configuration;
   b) securing at least one end of the fabric to inhibit unraveling thereof;
   c) inserting the fabric in or on a molding structure of a first predetermined shape comprising a plurality of expanded volume segments joined together in a string by intermediate articulation members, the first predetermined shape being different from the braided configuration;
   d) heating the molding structure to an elevated temperature for a time sufficient to heat set the fabric in the first predetermined shape to retain the first predetermined shape when the medical device is in a relaxed state; and
   e) imparting a second predetermined shape to the metal fabric, comprising the first predetermined shape wound about itself, to retain the second predetermined shape when the medical device is in the relaxed state.

2. The method of claim 1, wherein the first predetermined shape comprises a plurality of generally spherical or ovaloid members joined together in the string.

3. The method of claim 2, wherein the second predetermined shape comprises a spiral winding of a plurality of coils.

4. The method of claim 3, wherein the spiral winding has alternating relatively small and relatively large diameter coils.

5. The method of claim 3, wherein the spiral winding includes a plurality of internal coils within a central opening of a plurality of external coils.

6. The method of claim 2, further comprising longitudinally stretching the string to reduce the transverse dimension of the string.

7. The method of claim 2, and further comprising a) providing a tubular delivery catheter having a proximal end, a distal end and a lumen extending there between; b) longitudinally stretching the string to reduce the transverse dimension of the string; and c) loading the string into the lumen of the delivery catheter.

8. The method of claim 1, wherein the imparting a second predetermined shape to the metal fabric comprises a) providing a molding element having the second predetermined shape; b) inserting the fabric with the first predetermined shape into or on the molding element having the second predetermined shape; c) heating the molding element to a temperature and for a time sufficient to heat set the medical device in the second predetermined shape.

9. The method of claim 1, wherein the imparting a second predetermined shape to the metal fabric comprises a) providing a wire strand of a shape memory metal of a length generally the same as that of said string; b) heat setting the wire strand to a shape corresponding to the desired second shape; and c) threading the string onto the wire strand.

10. The method of claim 9, wherein the wire strand is heat set into a spiral winding of a plurality of coils.

11. The method of claim 10, wherein the spiral winding has alternating relatively small and relatively large diameter coils.

12. The method of claim 10, wherein the spiral winding includes a plurality of internal coils within a central opening of a plurality of external coils.

13. The method of claim 9, wherein the wire strand is heat set into a shape such that the medical device assumes a spherical shape upon being threaded onto the wire strand.

14. The method of claim 9, further comprising longitudinally stretching the string to reduce the transverse dimension exhibited by the second predetermined shape.

15. The method of claim 9, further comprising:
a) providing a tubular delivery catheter having a proximal end, a distal end and a lumen extending there between;
b) longitudinally stretching the string to reduce the transverse dimension of the string; and
c) loading the string into the lumen of the delivery catheter.

16. The method of claim 9, further comprising affixing a clamp to the wire strand and to the metal strands comprising the fabric at one end only of the metal strands.

17. The method of claim 1, wherein the metal strands are super elastic alloys and have a diameter in the range of from 0.001 to 0.006 inch.

18. The method of claim 1, wherein the tubular metal fabric comprises a pair of opposed ends, and wherein the securing at least one end of the fabric to inhibit unraveling thereof comprises affixing a clamp member to one of said opposed ends.

19. The method of claim 18, further comprising affixing a clamp member separately to both of said opposed ends.

20. The method of claim 18, wherein the clamp member includes means for releasably attaching it to a delivery device.

21. A medical device for use in occluding a vessel, channel, lumen or cavity in the circulatory system of a human or animal comprising:
a braided tubular fabric comprising a braided configuration formed of a plurality of braided metal strands of a shape memory alloy,
said braided tubular fabric further comprising:
(a) a first preset shape different than the braided configuration, wherein the first preset shape comprises a plurality of expanded volume segments joined together in a string by intermediate articulating members of a lesser cross-sectional dimension than that of the expanded volume segments; and
(b) a second preset shape, the second preset shape comprising the first preset shape wound about itself, wherein the second preset shape is retained when the medical device is in a relaxed, unstressed state.

22. The medical device of claim 21, wherein the second preset shape comprises said string shaped into a spiral.

23. The medical device is claim 21, wherein the second preset shape comprises said string formed as a spiral of a plurality of coils of alternating first and second diameters.

24. The medical device of claim 21, wherein the second preset shape comprises said string formed as a spiral winding that includes a plurality of internal coils within a central opening of a plurality of external coils.

25. The medical device as in claim 21, wherein the second preset shape has comprises said string formed to conform to the shape of a vascular cavity to be filled.

26. The medical device of claim 21, wherein said string is threaded onto a shape defining wire.

27. The medical device of claim 26, wherein the shape defining wire is a metal alloy exhibiting shape memory properties.

28. The medical device of claim 27, further comprising means for gathering and securing an end of the braided metal strands to prevent unraveling of the braided tubular fabric and wherein the shape defining wire is also secured by the means for gathering and securing.

29. The medical device as in claim 28, wherein the means for gathering and securing is a clamp affixed to a proximal end of the medical device.

30. The medical device of claim 29, wherein the clamp includes a threaded connection for attachment to a delivery device.

31. The medical device as in claim 30, further comprising a second clamp affixed to a distal end of the string.

32. The medical device as in claim 21, wherein at least one of the expanded volume segments contains a polyester fabric.

33. The medical device of claim 21, further comprising a shape memory wire disposed within the braided tubular fabric and coupled to the braided tubular fabric at only one location.

34. The medical device of claim 33, wherein the shape memory wire is heat treated into the second preset shape.

35. The medical device of claim 33, wherein the tubular fabric is configured to be elongated to a greater length than the shape memory wire for delivery to a target site.

36. The medical device of claim 33, wherein the shape memory wire is disposed coaxially within the braided tubular fabric.

37. The medical device of claim 21, wherein the second preset shape has a larger cross-sectional dimension than the first preset shape.

38. The medical device of claim 21, wherein the first preset shape comprises at least three expanded volume segments joined together in a string by intermediate articulating members of a lesser cross-sectional dimension than that of the expanded volume segments.

39. The medical device of claim 21, wherein the first preset shape comprises a plurality of generally spherical or ovaloid members joined together in the string.

40. The medical device of claim 21, wherein said braided tubular fabric is configured to be constrained to reduce a transverse dimension of both the first preset shape and the second preset shape, and wherein said braided tubular fabric is further configured to return to the first preset shape and the second preset shape when unconstrained.

* * * * *

UNITED STATES PATENT AND TRADEMARK OFFICE
CERTIFICATE OF CORRECTION

| | |
|---|---|
| PATENT NO. | : 8,361,138 B2 |
| APPLICATION NO. | : 11/881026 |
| DATED | : January 29, 2013 |
| INVENTOR(S) | : Adams |

It is certified that error appears in the above-identified patent and that said Letters Patent is hereby corrected as shown below:

In the Claims:

Column 14,
Line 11, "shape has comprises" should read --shape comprises--.

Signed and Sealed this
Eleventh Day of June, 2013

Teresa Stanek Rea
*Acting Director of the United States Patent and Trademark Office*